United States Patent [19]

Grandi

[11] Patent Number: 4,626,510

[45] Date of Patent: Dec. 2, 1986

[54] **PLASMIDIC VECTORS FOR EXPRESSING IN *BACILLUS SUBTILIS* AND A METHOD OF PREPARING THEM**

[75] Inventor: Guido Grandi, Segrate, Italy

[73] Assignee: Eni-Ente Nazionale Idrocarburi, Roma, Italy

[21] Appl. No.: 528,098

[22] Filed: Aug. 31, 1983

[30] Foreign Application Priority Data

Sep. 8, 1982 [IT] Italy ............................... 23166 A/82

[51] Int. Cl.$^4$ ..................... C12N 1/00; C12N 15/00; C12P 21/00
[52] U.S. Cl. .................. 435/317; 435/172.3; 435/91; 435/68; 935/27; 935/74; 935/73
[58] Field of Search .................. 435/68, 172.3, 317

[56] References Cited

U.S. PATENT DOCUMENTS 4,430,434 2/1984 Sanders et al. ..................... 435/253

FOREIGN PATENT DOCUMENTS 0063953 11/1982 European Pat. Off. ......... 435/172.3

OTHER PUBLICATIONS

Maniatis et al., 1982 *Molecular Cloning: A Laboratory Manual* Cold Spring Harbor Laboratory pp. 3 and 5.
Weisblum et al., 1979 "Plasmid Copy Number Control: Isolation and Characterization of High-Copy Number Mutants of pE194. *J. Bact.* v137(1), pp. 635-643.

*Primary Examiner*—Thomas G. Wiseman
*Assistant Examiner*—Joanne M. Giesser
*Attorney, Agent, or Firm*—Hedman, Gibson, Costigan & Hoare

[57] ABSTRACT

A special description is given of plasmids pSM15, pSM16 and pSM17, which are hybrid plasmids derived by coupling pUB110 and modified pE194. The described plasmids are cloning vectors in *Bacillus subtilis* and are characterised by a marker of resistance to Kanamycin and an EcoRI site located near the end of the ribosome recognition sequence; they can also be used to induce the coded heterologous protein from cloned DNA with sub-inhibiting doses of erythromycin.

These plasmids are prepared via the formation of plasmids pSM4, pSM5 or pSM6, which can be expressed either in *B. subtilis* or in *E. coli*.

11 Claims, 7 Drawing Figures

5'- GAGCTCGTGCTATAATTATACTAATTTTATAAGGAGGAAAAAAATATGGGCATTTTTAGTATTTTGTAATCAG
      promoter

CACAGTTCATTATCAACCAAACAAAAAAATAAGTGGTTATAATGAATCGTTAATAAGCAAAATTCATATATAACCAAATT pSM4=pSM15    GGAATTCC
                    pSM5=pSM16    TTAGGAATTCC
                    pSM6=pSM17   TTATGGAATTCC
          AAAGAGGG
            S.D.
                                          AACAAAGAATACAAGAAAATA — 3'

PLASMIDIC VECTORS FOR EXPRESSING IN *BACILLUS SUBTILIS* AND A METHOD OF PREPARING THEM

DESCRIPTION

The invention relates to novel plasmidic vectors for expressing high levels of coded protein products from heterologous DNA in *Bacillus subtilis*.

As is known, fragments of DNA from eucaryotic and procaryotic organisms coding certain proteins can be isolated and inserted into micro-organisms for the purpose of replication, transcription and translation thereof.

According to U.S. Pat. No. 4,237,224, a process for preparing biological chimeras comprises the following:

(i) Cutting the heterologous DNA, using an appropriate restriction enzyme;

(ii) Inserting the resulting fragments, using a second enzyme called ligase, into a vector, which has been cut by the same enzyme;

(iii) Transferring the resulting hybrid molecules to host cells by the mechanism of transformation, conjugation or transfection and finally (iv) Screening the resulting clones, so as to identify those bearing the coding DNA for the particular protein of interest.

It is also known that in order to synthesize a given protein, the cell requires specific sequences (the promoter and the Shine-Dalgarno) present on the DNA, which enable the RNA polymerase to transcribe the DNA into mRNA and enables the corresponding ribosomes and enzymes to translate the mRNA into proteins.

Since these recognition sequences may differ from one organism to another, the best method of expressing a heterologous protein in a given host cell is to place the structural gene of the protein under the control of recognition sequences specific to the host cell.

With regard to the molecular biology of *Escherichia coli*, there are numerous known publications (e.g. references 1 and 2) which show the ease of expressing at high levels of heterologous proteins once the codifying genes have been placed under the control of sequences which are well recognized by the transcription and translation system of the host cell.

However, in view of the pathogenic character of the aforementioned micro-organism, products obtained therefrom are of little or at least doubtful use in sectors such as pharmaceuticals or food.

It is therefore desirable to express heterologous genes in *Bacillus subtilis*, an organism which does not have the aforementioned disadvantages of *E. coli* and is therefore of high industrial importance.

Accordingly, the invention relates to novel vectors which can be used for synthesizing heterologous proteins in *Bacillis subtilis*; the invention also covers bifunctional plasmids capable of being expressed either in *B. subtilis* or *E. coli* and of use in preparing the aforementioned vectors.

The previously-mentioned aim is obtained by a method using a plasmid originally isolated in *Staphylococcus aureus*, after suitable modification which is an integral part of the present invention.

The plasmid in question (pE194) has been extensively studied and its primary structure has been determined (refs. 3, 4, 5, 6, 7 and 8). It contains extremely active recognition sequences for the transcription and translation system (refs. 5, 7 and 8) which can be used to synthesize a methylase which gives resistance to erythromycin. Plasmid pE194 has been modified as mentioned relative to the plasmid known in the literature (this is a first important feature of the invention) in that the promoter and the Shine-Dalgarno sequence of the methylase gene have been used as the recognition point of RNA polymerase and ribosomes respectively, for synthesizing heterologous proteins in *E. coli* and *B. subtilis*.

It is thus possible, by constructing a restriction site just after the sequence recognized by the ribosomes, to insert a given gene which will thus be expressed under the control of the promoter and the Shine-Dalgarno sequence of the gene giving resistance to erythromycin. In addition, as in the case of methylase (refs. 4 and 5) the coded heterologous protein can be synthesized from the cloned gene by exposing the cells to subinhibiting doses of erythromycin.

Plasmid pE194 modified as described can be used to obtain hybrid plasmids derived by coupling pE194 to plasmids pUB110 and pBR322. These hybrid plasmids are the main object of the present invention.

Some of the most important of these are plasmids pSM15, pSM16 and pSM17, which are vectors for cloning in *Bacillus subtilis* and are characterised by a Kanamycin resistance marker by means of which they can be selected, and an EcoRI site located near the end of the ribosome recognition sequence. At this site, DNA fragments obtained from heterologous DNA can be cloned after cutting with EcoRI. Likewise, by treating the vectors with S1 enzyme after linearization with EcoRI, it is possible to clone fragments obtained from any enzyme (i) "blunt end" or (ii) "sticky end" after treatment with S1 or Pol I of *E. coli*.

Another feature of the plasmids is that the coded heterologous protein can be induced from cloned DNA by using sub-inhibiting doses (0.02 µg/ml) of erythromycin to obtain hyperproduction.

Plasmid pSM15 is described in FIG. 1 and FIG. 2 shows the process of preparation.

The sequences of the modified region into which the EcoRI site has been inserted are shown in FIG. 7, which also shows the differences between plasmids pSM16 and pSM17 compared with plasmid pSM15.

As stated, the plasmids described here are vectors for cloning heterologous DNA and facilitate incorporation of the desired genes in the host cell; the following cloned genes are particularly important: β-lactamase, iso-amylase and dehydrofolic reductase.

The plasmids according to the invention are obtained by a method in which the starting materials are plasmids pE194 and pBR322 extracted respectively from strains of *Bacillus subtilis* BD170 (ref. 4) and *Escherichia coli* HB101 (ref. 9), both easily obtainable at any molecular biology laboratory. In addition, plasmid pBU110 is used during the process and is described in reference 4.

The essential part of the method, apart from the initial modification of plasmid pE194, is the preparation and isolation of plasmids pSM4 (FIG. 3), pSM5 and pSM6, which are capable of being expressed either in *B. subtilis* or *E. coli* and are therefore important intermediates for finally obtaining plasmids pSM15, pSM16 and pSM17.

The previously-mentioned and other Figures show the sites at which the various restriction enzymes cut the plasmids. The main sites, apart from EcoRI, are BamHI, HindIII, XbaI and SstI, all capable of linearizing plasmids having a single recognition site.

Other objects of the invention will become apparent to those skilled in the art from the above description taken in connection with the accompanying drawings wherein:

FIG. 6 is a schematic illustration of the reduction of the length of a linear DNA fragment by the combined action of the ExoIII and SI enzymes;

FIG. 7 is a schematic illustration of the pE194 fragment containing the promoter and the Shine-Dalgarno sequence and of its modification to pSM15, pSM16 and pSM17.

Figure 1:
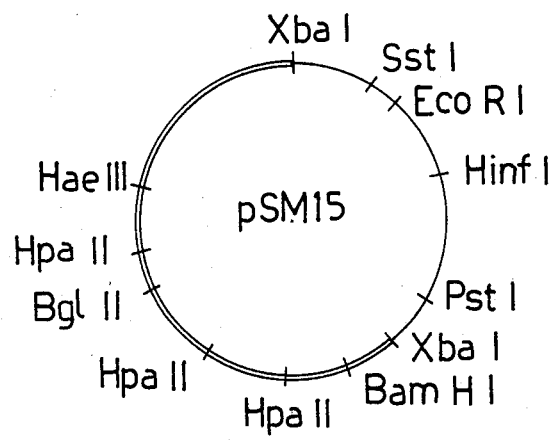
FIG. 1 is a restriction map of plasmid pSM15.
Figure 3:
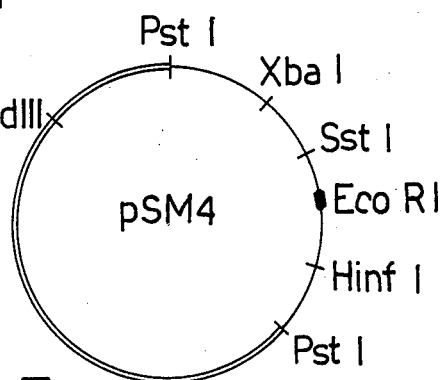
FIG. 3 is a restriction map of plasmid pSM4.

An *E. coli* strain HB101 harboring pSM6 and an *E. coli* strain SMS108 harboring pSM17 have been deposited with the American Type Culture Collection and given the respective ATCC accession numbers 53352 and 53353.

1. Preparation of plasmids pE194 and pBR322

The BD 170 (pE194) strain of *B. subtilis* and the HB101 (pBR322) strain of *E. coli* were each used to inoculate 1 liter of LB (10 g/l Tryptone, 5 g/l yeast extract, and 10 g/l Nacl). The cells were harvested by centrifuging at 5,000 rpm for 10 minutes, after growing overnight at 32° C. and 37° C. respectively.

The cells were washed by re-suspending them in half the initial volume with a solution of 25% sucrose, 0.1M NaCl and 0.05M Tris-Cl(pH 7.5) and were re-centrifuged and re-suspended in a tenth of the initial volume (100 ml) of the same solution. Then, after adding lysozyme to a final concentration of 0.5 mg/ml the cells were incubated at 37° C. for 15 minutes. Finally, to each of the two tubes containing 100 ml of cellular re-suspension, the following were added in the following order: 24 ml 5M NaCl, 6 ml 0.5M EDTA at pH 8.5 and 130 ml of 2% SDS, followed by 0.7M NaCl. The mixture was kept at 4° C. overnight.

The next day the solutions were centrifuged at 8000 rpm in a Sorvall GSA rotor for 45 minutes and one tenth by volume of a 3M solution of sodium acetate and 2 volumes of 95% ethanol were added to the supernatant fluid.

The solutions were kept at −20° C. for 3 hours and then centrifuged in a Sorvall GSA rotor at 8000 rpm for 30 minutes.

The pellets were re-suspended in TES (30 mM Tris-Cl pH 7.5, 50 mM NaCl and 5 mM EDTA), obtaining a final volume of 24 ml for preparation either of pE194 or pBR322. Next, each preparation was divided among 4 tubes each containing the following: 6 ml of plasmidic solution, 2 ml ethidiur bromide 1 mg/ml and 7.35 g cesium chloride.

The tubes were centrifuged at 40 000 rpm for 40 hours in a Beckman 70Ti rotor.

At the end of the process, each tube showed two clearly-visible (in UV light), distinct bands, one representing chromosomal DNA whereas the lower band represented plasmidic DNA.

The lower bands were extracted with a syringe and the solutions were washed 4 times with isopropyl alcohol and extensively dialyzed against TE buffer (10 mM Tris-Cl and 1 mM EDTA, pH 8.0).

Finally the two plasmidic DNA's were precipitated in ethanol at 31 10° C. after adding to each solution one tenth by volume of a 3M sodium acetate solution and 2 volumes of 95% ethanol.

After centrifuging at 10 000 rpm in a Sorvall SS 34 rotor for 30 minutes, the pellets were washed with 70% ethanol, dried and re-suspended in TE buffer to obtain a plasmid solution of 100 μg/ml.

2. Preparation of pE194-pBR322 hybrid plasmid

1 μg of pE194 and 1.4 μg of pBR322 were mixed and linearized with PstI restriction enzyme, obtained from BRL and used as specified by the manufacturer, after which the reactions were stopped by adding an equal volume of phenol saturated with TE buffer. After agitation, the phenol present in the aqueous phase was extracted three times with ether, after which the DNA was precipitated at −70° C. for 10 minutes after adding one tenth by volume of 3M sodium acetate and 2 volumes of 95% ethanol. The DNA was re-suspended in 100 μl of a solution containing 50 mM Tris-Cl(pH 7.6), 10 mM $MgCl_2$, 10 mM dithiothreitol and 15 μM ATP. Next, 0.05 U of T4 ligase prepared as per Weiss (10) were added and the reaction was continued at 10° C. for 4 hours.

5 μl of the mixture of ligase was used to transform cells of *E.coli* HB101 suitably treated with 0.1M $CaCl_2$ solution (11).

Selection was made by placing 0.1 ml of transformed cells on plates containing L agar+15 μg/ml tetracycline, after which a check was made that the colonies were sensitive to Ampicillin (since a cut with a PstI in pBR322 inactivates β-lactamase which gives resistance to ampicillin, the insertion of a DNA molecule at the PstI site of pBR322 inactivates β-lactamase).

Plasmids from six $Tc^R$, $Amp^S$ colonies were purified as follows:

1 ml of O.N. culture of each clone was centrifuged for 1 minute in a type 5414 Epperdorf centrifuge. The cells were re-suspended in 1 ml of 25% sucrose, 0.1M NaCl and 0.05M tris-Cl pH 7.5 and re-centrifuged.

The cells were then re-suspended in 100 μl of the same solution containing 0.5 mg/ml lysozyme and incubated at 37° C. for 15 minutes. The following were then added in the following order: 24 μl of a solution of 5M NaCl, 6 μl of 0.5M EDTA pH 8.5 and 135 μl of 2% SDS, 0.7M NaCl. The solutions were preserved at 4° C. for 3 hours and then cold centrifuged for 15 minutes in a 5414a Epperdorf centrifuge.

After adding 2 μl of a solution of pancreatic RNAse (10 mg/ml), the supernatant liquids were incubated at 37° C. for 15 minutes. Next, 10 μl of 10 mg/ml pronase predigested at 37° C. for half an hour were added and the samples were re-incubated at 37° C. for 2 hours.

Finally, one tenth by volume of 3M sodium acetate and 2 volumes of 95% ethanol were added to the samples and the DNA's were precipitated at −70° C. for 10 minutes.

After centrifuging, the pellets were dried and then re-suspended in 40 μl of PstI enzyme reaction buffer (20 mM Tris-Cl pH 7.5, 10 mM of $MgCl_2$, and 50 mM ammonium sulphate). After adding one unit of enzyme and incubating at 37° C. for one hour, the samples were placed on 0.8% agarose gel and the DNA's were separated by applying a potential difference of 30 V for 15 hours.

The gel was coloured with 0.5 γ/ml solution of ethidium bromide, showing that all six analyzed colonies carried a plasmidic DNA which, after digestion with PstI, gave two distinct bands which migrated with the linearized molecules of pE194 and pBR322.

This showed that the plasmids were really made up of pE194 and pBR322 bonded together at the PstI site. Two clones taken at random from the six were subsequently studied to analyze the orientation of the pE194 molecules relative to the pBR322.

To this end, the plasmidic DNA extracted from the two clones was linearized with HindIII enzyme, which cuts in the pBR322 region at a distance of 783 BP from the PstI site, and will then cut with SstI, which cuts in the pE194 at a distance of 1059 BP from the PstI site. Depending therefore on the orientation of pE194 relative to pBR322 as a result of double digestion, we should expect the appearance of two bands on the agarose gel, the molecular weights being $3.14 \times 10^6$ and $2.2 \times 10^6$ or $4.1 \times 10^6$ and $1.3 \times 10^6$.

Analysis on the agarose gel showed that one clone bore a plasmid which, after being cut with HindIII and SstI, gave two DNA fragments of molecular weight $3.20 \times 10^6$ and $2.32 \times 10^6$, whereas the other clone had a plasmidic DNA which after similar digestion gave rise to two fragments weighing $4.20 \times 10^6$ and $1.32 \times 10^6$.

Figure 4:
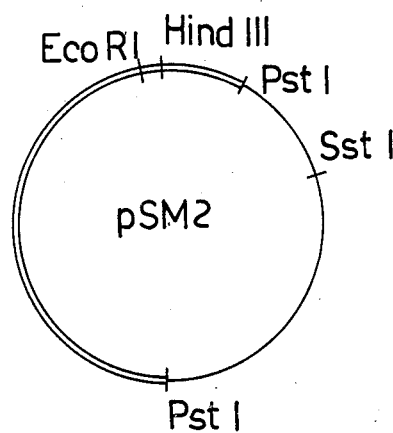
FIG. 4 is showing the different orientation of the pE194 fragment in respect of pBR322 in the plasmids pSM1 and pSM2.
Figure 4:
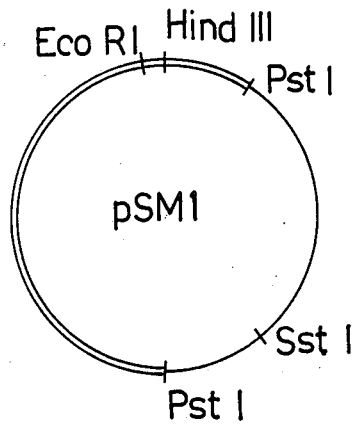
Figure 2:
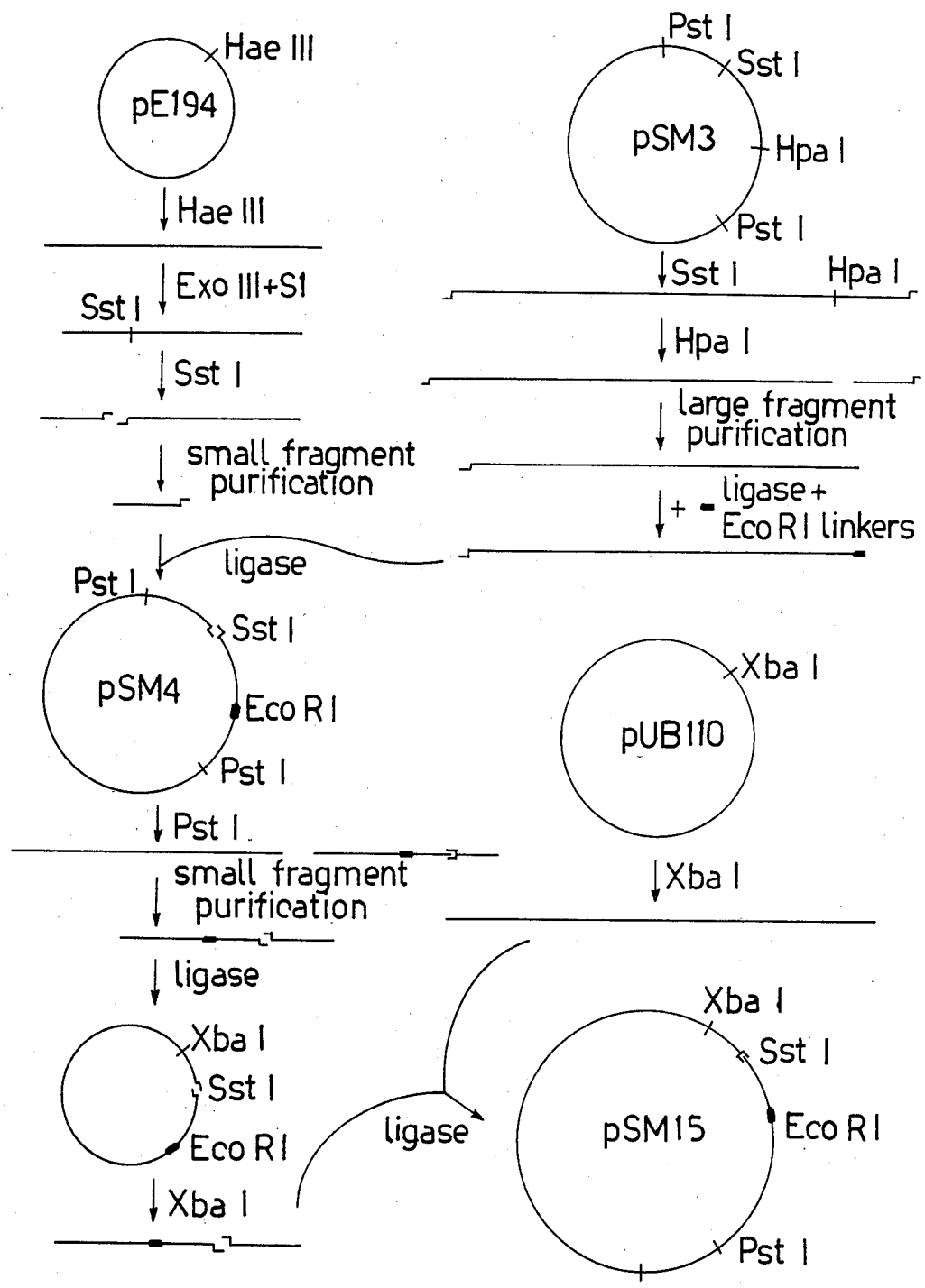
FIG. 2 is a schematic illustration of the construction of plasmid pSM15.

This indicated that the two plasmids, named pSM1 and pSM2, had different orientations (FIG. 4).

3. Elimination of the EcoRI site on plasmid pSM2

Plasmid pSM2 bears a single EcoRI site in the pBR322 region (FIG. 4). In order to eliminate it, 1 μg of pSM2 (10 μl) was digested with 1 unit of EcoRI enzyme in 30 μl of a solution of 100 mM Tris-Cl pH 7.5, 5 mM MgCl₂, 2 mM mercaptoethanol and 50 mM NaCl for one hour at 37° C.

The enzyme was inactivated by adding 30 μl of phenol saturated with TE. After the phenol had been eliminated from the aqueous phase and the DNA had been precipitated by the previously-described method, the linearized plasmid was re-suspended in 40 μl of a solution of 10 mM NaOAC-HOAC pH 4.13, 300 mM NaCl and 12 mM ZnSO₄, after which 2 μl of enzyme S1 (11.7 U/μl) were added.

The enzyme was reacted at 15° C. for 1 hour and then activated by adding a drop of phenol.

After the phenol had been eliminated by three extractions with ether, the DNA was precipitated at −70° C. for 10 minutes by adding 4 μl of 3M NaOAC and 100 μl of 95% ethanol.

The pellet obtained after centrifuging in an Epperdorf 5414 centrifuge for 10 minutes, was dried and re-suspended in 40 μl of a solution of 50 mM Tris-Cl pH 7.5, 10 mM MgCl₂, 10 mM dithiothreitol, and 50 μM ATP.

One unit of T4 ligase was added to the solution and the reaction was continued at 10° C. for 12 hours.

After the enzyme had been inactived at 65° C. for 10 minutes, 5 μl of the reaction mixture were used to transform 100 μl of cells of E. coli HB101 which had been suitably treated as previously described.

The transformation yielded 44 Tc$^R$ clones.

Three of these clones were subsequently analyzed and, after extraction of 1 ml of culture from the plasmid, using the previously-described method of rapid extraction, two of the clones were found to bear a plasmid which, after digestion with EcoRI enzyme, did not change from the helical to the linear form, and thus indicated loss of the EcoRI site.

Figure 5:
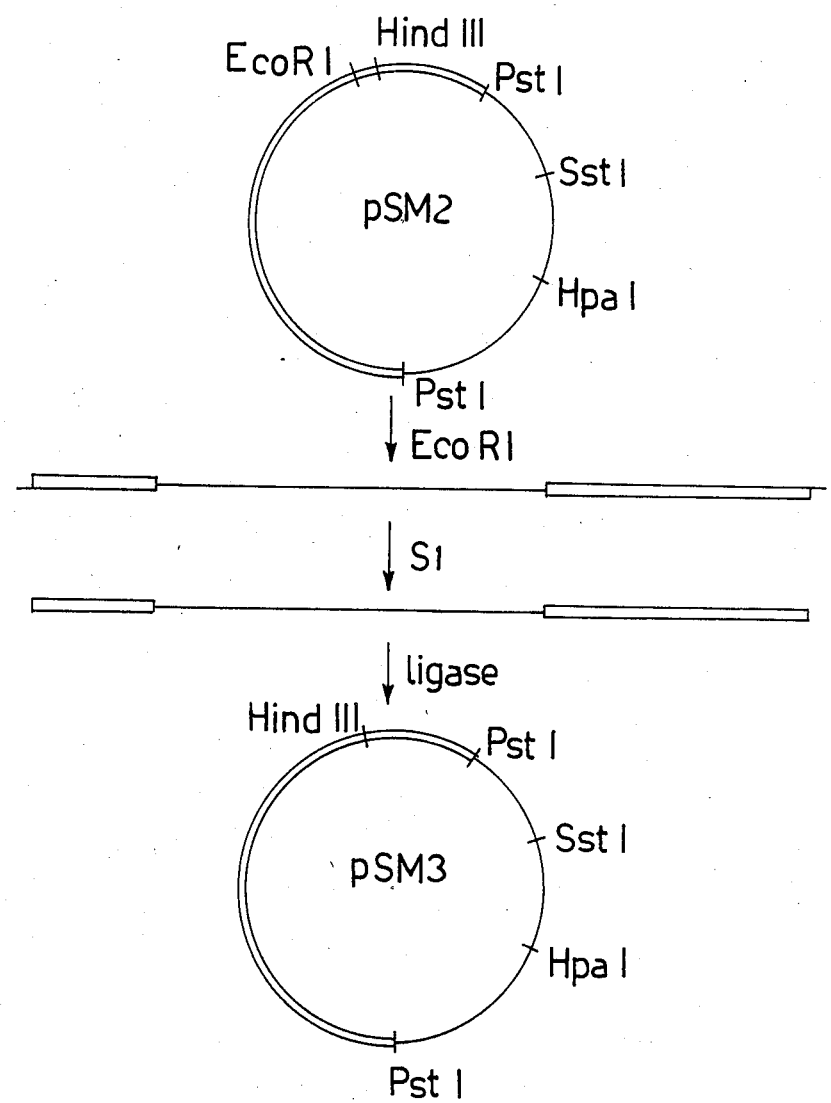
FIG. 5 is a schematic illustration of the construction of plasmid pSM3 from pSM2.

One of these plasmids, after being purified by 1 liter of culture, was called pSM3 (FIG. 5).

4. Isolation of the HpaI-SstI fragment of pSM3

As FIG. 5 shows, pSM3 has a single HpaI site and a single SstI site, both in the pE194 region.

pSM3 DNA cut with these restriction enzymes generates two fragments, of molecular weight $5 \times 10^5$ and $4.83 \times 10^6$.

7 μg of pSM3 DNA, purified by the previously-described method with pE194 and pBR322, were cut with 7 U of HpaI enzyme using the buffer recommended by the supplier (BRL) in 100 μl of final solution at 37° C. for 1 hour and then, after the enzyme had been inactivated at 65° C. for 10 minutes, the following were added: 1.8 μl of 5M NaCl, 3 μl of concentrated mercaptoethanol and 7 units of SstI. The reaction was continued at 37° C. for 1 hour and then the enzyme was again inactivated at 65° C. for 10 minutes.

The DNA was treated with phenol saturated with TE buffer and precipitated by adding one tenth by volume of 3M sodium acetate and 2 volumes of 95% ethanol at −70° C. The precipitate was dried and then re-suspended in 300 μl of 30 mM Tris-Cl pH 8.1, 1 mM EDTA and 1M NaCl.

The sample was then placed on 5 ml of a 5-20% gradient of sucrose and centrifuged at 40 000 rpm for 7.4 hours in a Beckman Sw 55.1 rotor.

Next, 23 fractions, each of 6 drops, were collected and 15 μl of each fraction was analyzed on 0.8% agarose gel. Fractions 16-21 were found to possess almost all the large HpaI-SstI fragments. These were harvested together, the pool was diluted with an equal volume of H₂O and the DNA was precipitated at −20° C. for 14 hours after adding 2 volumes of 95% ethanol.

After centrifuging at 10,000 rpm in a Sorvall SS34 rotor for 30 minutes, the pellet was washed with 70% ethanol, dried and re-suspended in TE to obtain a final DNA concentration of 100 μg/ml.

5. Attaching a linker to the SstI-HpaI fragment

In the illustrated example, use was made of the linker bearing the EcoRI site. 1 μg of SstI-HpaI fragment (10 μl) was used for attaching the

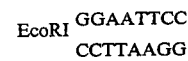

linker at its "blunt end". The EcoRI linker in an excess of 500 times the molarity relative to the fragment was added to 50 μl of reaction mixture containing 1 μg of fragment, 50 μM ATP, 50 mM Tris-Cl pH 7.5, 10 mM MgCl₂ and 10 mM dithiothreitol.

Next, 2 U of T4 ligase were added and the reaction was continued at 10° C. for 12 hours.

The enzyme was inactivated at 65° C. for 10 minutes.

6. Preparation of the pE194 DNA fragment bearing the "promoter" and "Shine-Dalgarno" sequences of the methylase gene The fragment was obtained, after eliminating all superfluous material from part III of the Shine-Dalgarno sequence by the following method:

10 μg of pE194 were digested in 150 μl final volume in 6 mM Tris-Cl pH 7.6, 6 mM MgCl₂, 6 mM mercaptoethanol and 10 units of HaeIII at 37° C. for 1 hour.

The enzyme was then inactivated by adding an equal volume of phenol saturated with TE. The phenol dissolved in the aqueous phase was eliminated by three extractions with ether, after which the DNA was precipitated at −70° C. for 10 minutes by adding 20 μl of 3M sodium acetate and 400 μl of 95% ETOH. After centrifuging in a 5414 Epperdorf centrifuge for 10 minutes, the pellet was washed with 100 μl of 70% ethanol and dried in vacuo.

The DNA was then re-suspended in 40 μl of 100 mM Tris-Cl pH 7.6 and 10 mM MgCl₂ and, after adding 4 μl of ExoIII (BRL, 25 units/μl) the reaction was continued at 20° C. for 16 minutes.

Under these conditions, about 8–10 bases per minute were eliminated from end 3' (FIG. 6).

The reaction was inactivated by adding 40 μl of a solution of 200 mM NaOAC-HOAC pH 4.13, 600 mM NaCl and 24 mM ZnSO₄.

Next, 3.5 μl of S1 enzyme (11.7 U/μl) were added and the reaction mixture was incubated at 15° C. for 2½ hours. The enzyme was inactivated by adding a drop of phenol subsequently extracted with ether.

The DNA was precipitated at −70° C. for 10 minutes after adding 9 μl of 3M NaOAC and 250 μl 95% ethanol, and was then centrifuged in a 5414 Epperdorf centrifuge.

The pellet was dried and re-suspended in 45 μl of TE. In order to eliminate contaminating salts, the solution was placed on a column of 1 ml of G-50 Sephadex, which had previously been dried by centrifuging at 2000 rpm.

The DNA was harvested by re-centrifuging the column at 2000 rpm for 2 minutes.

40 μl of solution were harvested and the following were added immediately: 5 μl of salts for SstI enzyme concentrated 10 times (salt 1X, 14 mM Tris-Cl pH 7.4, 6 mM MgCl₂, 90 mM NaCl, 2 mM marcaptoethanol) and 6 units of SstI enzyme (BRL).

After incubation at 37° C. for 1 hour, the enzyme was inactivated at 65° C. for 10 minutes.

The thus-treated DNA was placed on 7.5 acrylamide gel alongside pBR322 digested with HpaII as a standard of molecular weight, and was separated by applying a potential difference of 100 V for 3 hours. After the gel had been covered with a solution of 0.2 μg/ml ethidium bromide and displayed in UV light, the DNA sample, as expected, gave a series of bands which were very difficult to resolve and varied from about 130 to about 180 pairs of bases, and a series of bands having a much higher molecular weight.

Since the distance of the SstI site from the end of the ribosome recognition sequence (—GTT) is 157 BP+4 single bases ("sticky end" of cut with SstI), the gel region between the 13th and the 14th band generated by cutting pBR322 with HpaII (160 and 147 pairs of bases respectively) was cut with a razor-blade.

The DNA in the cut gel fraction was eluted with 0.8 ml of a solution of 10 mM Mg acetate, 0.5M NH₄ acetate, 0.1 SDS and 0.1 mM EDTA at 65° C. for 14 hours, as described by Maxam and Gilbert (16).

2 ml of 95% ethanol were added to 0.8 ml of solution and the DNA was precipitated at −20° C. for 24 hours.

After centrifuging at 10 000 rpm in a Sorvall SS34 rotor for 30 minutes, the pellet was washed with 0.5 ml of 70% ethanol, dried in vacuo and re-suspended in 0.5 ml TE. The ethidium bromide remaining in the DNA double helix was eliminated by extracting it four times with 1-butanol. At the end of extraction with alcohol, the final volume of aqueous solution was 160 μl.

18 μl of a 3M solution of NaOAC, 2 μl of 1M MgCl₂ and 400 μl of 95% ethanol were added.

The DNA was preciitated at −70° C. for 10 minutes and centrifuged for 10 minutes in an Epperdorf 5414 centrifuge.

After washing the pellet with 100 μl of 70% ethanol and drying in vacuo, the DNA was re-suspended in TE, bringing it to a concentration of 100 μg/ml.

7. Bonding the pE194 fragment to the HpaI-SstI fragment of pSM3 and transformation 0.1/μg of pE194 fragment purified as described in section 6 was bonded to 1 μg of HpaI-SstI fragment of pSM3 (section 5) in 50 μl of ligase mixture containing 50 mM Tris-Cl pH 7.5, 10 mM MgCl₂, 10 mM dithiothreitol and 50 μM ATP with 4 units of ligase T4 enzyme.

After 4 hours incubation at 10° C., 10 μL of ligase mixture were diluted 10 times in the same buffer and, after adding another 4 units of T4 ligase, the reaction was continued at 4° C. for a further 20 hours.

The enzyme was inactivated at 65° C. for 10 minutes.

10 μl of the dilute ligase mixture was used to transform 100 μl of suitable HB101 cells, prepared as previously described, selecting for resistance to tetracycline (Tc$^R$) on a plate of L agar+15 μg/ml of Tc.

Out of the 486 clones obtained, 30 were used to prepare the plasmid by the previously-described rapid procedure (see Section 2). After precipitation with ethanol, each pellet was re-suspended in 40 μl of EcoRI buffer 1×(100 mM Tris-Cl pH 7.5, 5 mM MgCl₂, 50 mM NaCl and 2 mM mercaptoethanol) and the DNA's were incubated at 37° C. for 30 minutes after adding one unit of EcoRI in each case. After the enzyme had been inactivated at 65° C. for 1 minute the samples were placed on 0.8% agarose gel and separated at a voltage of 30 V for 14 hours. The gel was then coloured for 15 minutes in a solution of 0.5 μg/ml ethidium bromide and displayed in UV light. 21 of the resulting 30 plasmids were "linearised" after treatment with EcoRI enzyme showing the presence of the EcoRI site in their sequence.

Plasmids were prepared as previously described from 1 liter of culture from 10 of these clones which were shown to have acquired the EcoRI site.

All the plasmids were analyzed with a set of restriction endonucleases (PstI, SstI, EcoRI, HpaI) and compared with plasmids pSM2, pBR322, pE194.

After being cut with PstI, all the plasmids gave two fragments, the larger of which migrated on the agarose gel with the linearized pBR322, whereas the smaller migrated slightly less fast than the pE194, as expected.

In addition, 10 plasmids were cut with SstI and EcoRI, giving two fragments, the larger of which migrated slightly more quickly than linearized pSM2 whereas the smaller was about 160 BP as expected.

The 10 plasmids were named pSM(4–13).

8. Sequence of the small EcoRI-PstI fragment of plasmids pSM4, pSM5, pSM6

The DNA of the hybrid plasmids obtained (e.g. pSM4, pSM5, etc) was doubly digested with EcoRI and PstI, generating three fragments easily separated on agarose gel. The smallest (BP 1220 approx.) bears the "promoter" and "Shine-Dalgarno" regions of the pE194 methylase genes.

In order to determine the distance between the "Shine-Dalgarno" and the EcoRI site (generated by the inserted linker), the fragment, after being purified with acrylamide gel as previously described (section 6) was cloned in M13 phage (a replicative double-helix form) and formed into sequences by the "dideoxynucleotides" method. There is no point in describing the procedure in detail, since it has already been extensively described (12, 13).

After the M13 phage had been cut with EcoRI and PstI, the following reaction mixture was prepared: 4 μl M13mp9 (0.01 pmols DNA), 4 μl EcoRI-PstI fragment of pSM4 (or pSM5, pSM6) (0.003 pmols of DNA). 2 μl of a solution of 500 mM Tris-Cl pH 7.5, 100 mM MgCl$_2$, 10 mM dithiothreitol, 2 μl mM ATP, 7 μl H$_2$O and 1 μl of T4 ligase (50 units/ml).

The reaction was carried out at 12.5° C. for 18 hours. 2-5 ng of DNA from the ligase mixture were used to transform cells of E. coli 71.18 (BRL) which had been suitably treated with CaCl$_2$ as previously described.

The white plaques bearing the phage in which the desired fragment had been inserted were selected on an YT agar plate (8 g Bacto-tryptone, 8 g Bacto Yeast Extract, and 5 g NaCl/l) after the following had been added to 0.3 ml of transformed cells:

0.2 ml cells of E. coli 71.18 in the exponential growth phase, 0.01 ml of IPTG (100 mM), 0.05 ml Xgal (2% in dimethyl formamide) and 3 ml of soft agar. The sequence of the region nearest the EcoRI site of the three plasmids pSM4, pSM5 and pSM6 is shown in FIG. 7.

As the data show, the EcoRI linker has been inserted in pSM4, pSM5 and pSM6 respectively at 0, 3 and 4 bases of distance from the last G of the sequence GAGGG, which is assumed to be that recognized by the 16 S ribosomal RNA and facilitates bonding the ribosomes to the RNA.

9. Elimination of the pBR322 sequence from plasmids pSM4, pSM5 and pSM6 and insertion of pUB∠in site XbaI 2 μg of DNA from pSM4, pSM5 and pSM6 were cut with PstI enzyme in 50 μl of a solution of 20 mM Tris-Cl pH 7.5, 10 mM MgCl$_2$ and 50 mM ammonium sulphate containing 2 units of PstI enzyme.

After 1 hour of incubation at 37° C., the enzyme was inactivated at 65° C. for 10 minutes.

All the reaction mixtures were placed on "low-melting" agarose gel and the DNA was separated by applying a potential difference of 30 V for 14 hours.

After colouring with ethidium bromide as previously described, the gel was exposed to UV light and all the three DNA's were found to be made up of two fragments, the larger of which migrated with the linearized pBR322 whereas the smaller had an electrophoretic mobility slightly greater than pE194.

The smaller fragments were eluted from the gel after removing the gel fraction containing them, by melting the agarose at 65° C. and double extracting with phenol. The DNA in the aqueous phase was twice precipitated in ethanol as previously described.

After drying the pellet, the DNA was re-suspended in TE at a final concentration of 20 μg/ml.

0.1 μg of this DNA was bonded with 0.05 units of T4 ligase in 20 μl of a solution of 50 mM tris-Cl ph 7.5, 10 mM MgCl$_2$, 10 mM dithiothreitol and 100 μM ATP.

After incubation at 12° C. for 18 hours, the enzyme was inactivated at 65° C. for 10 minutes.

The plasmids, which had been made circular, were then re-linearized by cutting them with 0.1 units of XbaI (which cuts at a single site in pE194) in 50 μl of a solution of 6 mM Tris-Cl pH 7.6, 0.1 M NaCl and 6 mM MgCl$_3$ for 1 hour at 37° C.

Finally after inactivation with phenol and precipitation with alcohol as previously described, the plasmid DNA's were bonded with plasmid pUB∠(14), which had been linearized with XbaI enzyme at a concentration of 100 μg/ml DNA in the ligase mixture.

The three ligase mixtures were used to convert cells of B. subtilis BD 170, suitably treated as described by Anagnostopoulus and Spizizen (15), by selection on plates of L agar containing 5 μg/ml of Kanamycin (Km).

Plasmids were extracted by the previously-described rapid method (Section 2) from 10 of the colonies obtained from each transformation, and the plasmids were cut with XbaI enzyme and compared with DNA from pUB110 cut with XbaI and with DNA from plasmids pSM4, pSM5 and pSM6 cut with PstI.

Those colonies which were found to possess a plasmid which, after cutting with XbaI, gave two fragments, the larger migrating with DNA from pUB110 linearized with XbaI and the smaller migrating with the small fragment of plasmids, pSM4, pSM5 and pSM6 cut with PstI were used to prepare plasmids from one liter of culture. These plasmids, called pSM15, pSM16 and pSM17, were analysed with various restriction enzymes and found to be made up as follows:

pSM15: pUB110+small PstI fragment of pSM4
pSM16: pUB110+small PstI fragment of pSM5
pSM17: pUB110+small PstI fragment of PSM6.

References

1. Robert T. M., Kacich R. and Ptashne M. (1979) Proc. Natl. Acad. Sci. USA 76, 760–764
2. Talmadge K. and Gilbert W. (1980) Gene 12, 235–241
3. Iordanescu S. (1976) Arch. Roum. Path. Exp. Microbiol 35, 111–118
4. Weisblum, B., Graham, M. Y., Gryczan T and Dubnau D. (1979) J. Bacteriol 137, 635–643
5. Shivakumar A. G., Hahn, J. and Dubnau D. (1979) Plasmid 2, 279–289
6. Shivakumar A. G., Hahn, J., Grandi, G., Kozlov, Y and Dubnau D (1980) Proc. Natl. Acad. Sci. USA 77, 3903–3907
7. Gryczan, T. J., Grandi, G., Hahn, J., Grandi R., and Dubnau D. (1980) Nucl. Ac. Res. 8, 6081–6097
8. S. Horinouchi et al—(1982) J. Bacteriol, 150, 804–814
9. Bolivar F., Rodriguez R., Betlach, M. C. and Boyer H. W. (1977) Gene 2, 75–93
10. Weiss, B et al (1968) J. Biol. Chem. 243, 4543–4555
11. Dagert, M., and Ehrlich, S. D. (1979) Gene 6, 23–28
12. Sanger, F., Nicklen, S., and Coulson, A. R. (1977) Proc. Natl. Acad. Sci. USA 74, 5463–5467
13. Messing, J., Crea, R. and Seeberg, P. H. (1981) Nucl., ac. Res. 9, 303–321
14. Gryczan, T. J., Contente, S., and Dubnau, D. J. Bacteriol (1978) 134, 318–329
15. Anagnostopoulus and Spizizien (1961) J. Bacteriol 81, 741–746
16. Maxam, A., and Gilbert, W. (1977) Proc. Natl. Ac. Sci. USA 74, 560–564
17. Kuhn, S., et al. (1979) Molec. Gen. Genet. 167, 235–241

I claim:

1. A hybrid plasmid that is useful for synthesizing heterologous proteins in *B. subtilis*, said hybrid plasmid being formed by coupling the plasmid pUB110 with the small PstI fragment of the plasmid pSM4, pSM5 or pSM6 at their XbaI sites, said hybrid plasmid having a marker of resistance to kanamycin and a EcoRI site located from 0 to 4 bases from the last G of the ribosome recognition sequence GAGGG, said hybrid plasmid being capable of producing the heterologous proteins coded by cloned DNA wherein said production is induced by subinhibiting doses of erythromycin.

2. Plasmid pSM15 according to claim 1 formed by coupling plasmid pUB110 with the small PstI fragment of plasmid pSM4.

3. Plasmid pSM16 according to claim 1 formed by coupling plasmid pUB110 with the small PstI fragment of plasmid pSM5.

4. Plasmid pSM17 according to claim 1 formed by coupling plasmid pUB110 with the small PsTI fragment of plasmid pSM6.

5. A hybrid plasmid pSM15 according to claim 1, formed by coupling the plasmid pUB110 with the small PstI fragment of the plasmid pSM4 at the XbaI site of pUB110, wherein the single EcorRi site is located at 0 bases from the last G of the ribosome recognition sequence GAGGG.

6. A hybrid plasmid pSM16 according to claim 1, formed by coupling the pUB110 plasmid with the small PstI fragment of the pSM5 plasmid at the XbaI site of pUB110, wherein the single EcoRI site is located 3 bases from the last G of the ribosome recognition sequence GAGGG.

7. A hybrid plasmid pSM17 according to claim 1, formed by coupling the pUB110 plasmid with the small PstI fragment of the pSM6 plasmid at the XbaI site of pUB110, wherein the single EcoRI is located 4 bases from the last G of the ribosome recognition sequence GAGGG.

8. A hybrid plasmid, capable of being expressed in *B. subtilis* and *E. coli* selected from the group consisting of pSM4, pSM5 and pSM6, said plasmid being obtained by:

(a) bonding together the plasmids pBR322 and pE194 at their Pst site to obtain plasmids pSM1 and pSM2, (b) eliminating the single EcoRI restriction site from the pBR322 region of the thus obtained pSM2 plasmid, which pSM2 plasmid is recognized in that it gives, after digestion with HindIII, two DNA fragments having a molecular weight of about $4.2 \times 10^6$ and $1.3 \times 10^6$, to obtain plasmid pSM3, (c) cleaving the pSM3 plasmid to separate the DNA fragment comprising a single HpaI and a single SstI site in the pE194 region, (d) attaching an EcoRI linker at the blunt end of the HpaI-SstI fragment, (e) separately obtaining the DNA fragment bearing the promoter and Shine-Dalgarno sequence of the methylase gene of plasmid pE194, and (f) bonding said separately obtained pE194 fragment to the HpaI-SstI fragment obtained according to step (d).

9. A hybrid plasmid that is useful for synthesizing heterologous proteins in *B. subtilis* and is selected from the group consisting of pSM15, pSM16 and pSM17, said plasmid being obtained by a process comprising:

(a) linearizing a plasmid selected from the group consisting of pSM4, pSM5 and pSM6 by digesting it with PstI restriction enzyme, obtaining thereby a large and a small PstI fragment;

(b) annealing the small PstI fragment having an electrophoretic mobility substantially corresponding to that of pE194, by means of T4 DNA ligase;

(c) linearizing by means of XbaI enzyme the plasmid obtained according to step (b) and the plasmid pUB110 and bonding together the linearized fragments at the XbaI site;

wherein the resultant hybrid plasmid has a marker of resistance to kanamycin and an EcoRI site located from 0 to 4 bases from the last G of the ribosome recognition sequence GAGGG and is capable of synthesizing the heterologous proteins coded by cloned DNA, which synthesis is induced using sub-inhibiting doses of erythromycin.

10. Hybrid plasmid pSM6 deposited with ATCC, under accession No. 53352.

11. Hybrid plasmid pSM17 deposited with ATCC, under accession No. 53353.

* * * * *